(12) United States Patent
Creedon et al.

(10) Patent No.: US 10,713,483 B2
(45) Date of Patent: Jul. 14, 2020

(54) PUPIL EDGE DETECTION IN DIGITAL IMAGING

(71) Applicant: Welch Allyn, Inc., Skaneateles Falls, NY (US)

(72) Inventors: William Niall Creedon, Portland, OR (US); Eric Joseph Laurin, Beaverton, OR (US); Richard Allen Mowrey, Ottawa (CA)

(73) Assignee: Welch Allyn, Inc., Skaneateles Falls, NY (US)

( * ) Notice: Subject to any disclaimer, the term of this patent is extended or adjusted under 35 U.S.C. 154(b) by 322 days.

(21) Appl. No.: 15/926,121

(22) Filed: Mar. 20, 2018

(65) Prior Publication Data

US 2019/0294858 A1 Sep. 26, 2019

(51) Int. Cl.
*G06K 9/00* (2006.01)
*G06T 7/12* (2017.01)
*H04N 5/232* (2006.01)

(52) U.S. Cl.
CPC .............. *G06K 9/0061* (2013.01); *G06T 7/12* (2017.01); *H04N 5/23229* (2013.01)

(58) Field of Classification Search
CPC .. G06K 9/0061; G06K 9/4652; G06K 9/6212; G06T 7/12; G06T 2207/30041; G06T 7/11; G06T 7/149; G06T 7/136; H04N 5/23229; A61B 3/00
See application file for complete search history.

(56) References Cited

U.S. PATENT DOCUMENTS

| | | | | |
|---|---|---|---|---|
| 5,291,560 A * | 3/1994 | Daugman | .......... | G06K 9/00906 382/117 |
| 5,751,836 A * | 5/1998 | Wildes | .............. | G06K 9/00597 382/117 |
| 5,859,686 A * | 1/1999 | Aboutalib | .............. | A61B 3/113 351/209 |
| 6,095,989 A * | 8/2000 | Hay | ..................... | A61B 3/0025 600/558 |
| 6,419,638 B1 * | 7/2002 | Hay | ..................... | A61B 3/0025 600/558 |
| 7,092,554 B2 * | 8/2006 | Chen | .................. | G06K 9/00268 382/118 |
| 7,377,643 B1 * | 5/2008 | Chock | ...................... | A61B 3/14 351/205 |
| 7,957,566 B2 * | 6/2011 | Suzuki | .............. | G06K 9/00604 382/117 |

(Continued)

FOREIGN PATENT DOCUMENTS

WO 2010-011785 1/2010

OTHER PUBLICATIONS

International Search Report and Written Opinion in PCT/US2019/022970 dated Jul. 4, 2019, 19 pages.

*Primary Examiner* — Xuemei G Chen
(74) *Attorney, Agent, or Firm* — Merchant & Gould P.C.

(57) ABSTRACT

A digital imaging system processes digital images of a subject's fundus and/or pupils to determine a pupil edge. Two regions of a digital image are evaluated to determine a threshold value. Typically, the two regions are selected such that each region would usually not include artifacts. The threshold value can then be used to identify a pupil-iris threshold in the digital image. Based on the pupil-iris threshold, pupil edges are identified.

20 Claims, 12 Drawing Sheets

(56) References Cited

U.S. PATENT DOCUMENTS

| | | | |
|---|---|---|---|
| 8,023,699 B2* | 9/2011 | Namgoong | G06K 9/0061 |
| | | | 382/115 |
| 8,768,014 B2* | 7/2014 | Du | G06K 9/0061 |
| | | | 382/117 |
| 8,867,825 B2* | 10/2014 | Ostermann | G06K 9/00986 |
| | | | 382/154 |
| 9,237,846 B2* | 1/2016 | Mowrey | A61B 3/0058 |
| 9,402,538 B2 | 8/2016 | Mowrey et al. | |
| 10,048,749 B2* | 8/2018 | Miao | G06K 9/033 |
| 10,445,574 B2* | 10/2019 | Odinokikh | G06K 9/00604 |
| 10,452,910 B2* | 10/2019 | Raducan | G06K 9/00597 |
| 2006/0110008 A1* | 5/2006 | Vertegaal | G06K 9/00604 |
| | | | 382/103 |
| 2011/0200235 A1 | 8/2011 | Tosa | |
| 2012/0013772 A1 | 1/2012 | Ishiga | |
| 2012/0201430 A1 | 8/2012 | Cambier | |
| 2016/0259961 A1 | 9/2016 | Vugdelija et al. | |
| 2018/0350070 A1* | 12/2018 | Ishii | G06T 7/0012 |

* cited by examiner

PUPIL EDGE DETECTION IN DIGITAL IMAGING

INTRODUCTION

Various types of abnormalities and diseases can be screened for by analyzing images captured by cameras. For example, photorefraction vision screening can evaluate whether a person has one or more types of refractive errors. In photorefractive vision screening, light from an external source enters the eye through the pupil and is focused to create a small illuminated spot on the retina. Some of the light from this retinal spot is returned out of the eye through the pupil after interaction with different layers of the retina. The pattern of light exiting the pupil is determined by the optics of the eye and is dominated by an examinee's refractive error (focusing errors of the eye).

As another example, fundus imaging can be used to screen for or monitor various diseases, such as diabetic retinopathy, hypertension, glaucoma, and papilledema. Trained medical professionals use cameras during eye examinations for disease screening. The cameras can produce images of the back of the eye and trained medical professionals use those images to diagnose and treat one or more diseases. These images are produced either with pharmacological pupil dilation, known as mydriatic fundus imaging, or without pharmacological pupil dilation, known as non-mydriatic fundus imaging. Because pupil dilation is inversely related, in part, to the amount of ambient light, non-mydriatic fundus imaging usually occurs in low lighting environments.

SUMMARY

Embodiments of the disclosure are directed to pupil edge detection in digital imaging. Generally, systems and methods disclosed herein process digital images and identify pupil edges in the digital images. Typically, a pupil-iris threshold value is determined and used to identify pupil edges.

In one aspect, a method of identifying a pupil edge in a digital image is disclosed. The example method includes receiving a digital pupil image; generating a mean first portion pixel intensity, including evaluating a first portion of the digital pupil image, generating a mean second portion pixel intensity including evaluating a second portion of the digital pupil image, averaging the mean first portion pixel intensity and the mean second portion pixel intensity, thereby generating an average pixel intensity, determining a modified standard deviation, generating a threshold value by summing the average pixel intensity and the modified standard deviation, and using the threshold value, identifying a pupil edge in the digital pupil image. Determining a modified standard deviation includes calculating a standard deviation of a pixel intensity for each pixel within the first portion and the second portion and multiplying the standard deviation by a multiplier.

In another aspect, a method for identifying a pupil in a digital image is disclosed. The example method includes: receiving a digital pupil image; identifying a first portion of the digital pupil image; identifying a second portion of the digital pupil image; determining a pixel intensity for each pixel within the first portion and each pixel within the second portion; determining a mean pixel intensity by calculating the mean of the pixel intensity for each pixel within the first portion and each pixel within the second portion; determining a modified standard deviation, including calculating a standard deviation of the pixel intensity for each pixel within the first portion and the second portion; and multiplying the standard deviation by a multiplier; generating a threshold value by summing the mean pixel intensity and the modified standard deviation; using the threshold value, identifying a pupil edge in the digital pupil image; and using the pupil edge, identifying the pupil in the digital pupil image.

In another aspect, a medical imaging system includes an illumination assembly including a near-infrared lighting unit, a digital camera assembly, a processing unit, and memory. The memory stores instructions that, when executed by the processing unit, cause the medical imaging system to: illuminate the near-infrared lighting unit; receive a digital image with the digital camera assembly; obtain a pixel grid size having a pixel grid width and a pixel grid length; generate a mean first portion pixel intensity, including evaluating a first portion of the digital pupil image, a first portion length being equal to the pixel grid length and a first portion width being equal to the pixel grid width; generate a mean second portion pixel intensity, including evaluating a second portion of the digital pupil image, a second portion length being equal to the pixel grid length and a second portion width being equal to the pixel grid width, average the mean first portion pixel intensity and the mean second portion pixel intensity, thereby generating an average pixel intensity; determine a modified standard deviation, including calculate a standard deviation of a pixel intensity for each pixel within the first portion and the second portion; and multiply the standard deviation by a multiplier; generate a threshold value by summing the average pixel intensity and the modified standard deviation; and using the threshold value, identify a pupil edge in the digital pupil image.

The details of one or more embodiments are set forth in the accompanying drawings and the description below. Other features, objects, and advantages of these embodiments will be apparent from the description, drawings, and claims.

DESCRIPTION OF THE FIGURES

The following drawing figures, which form a part of this application, are illustrative of described technology and are not meant to limit the scope of the disclosure in any manner.

DETAILED DESCRIPTION

Figure 1:
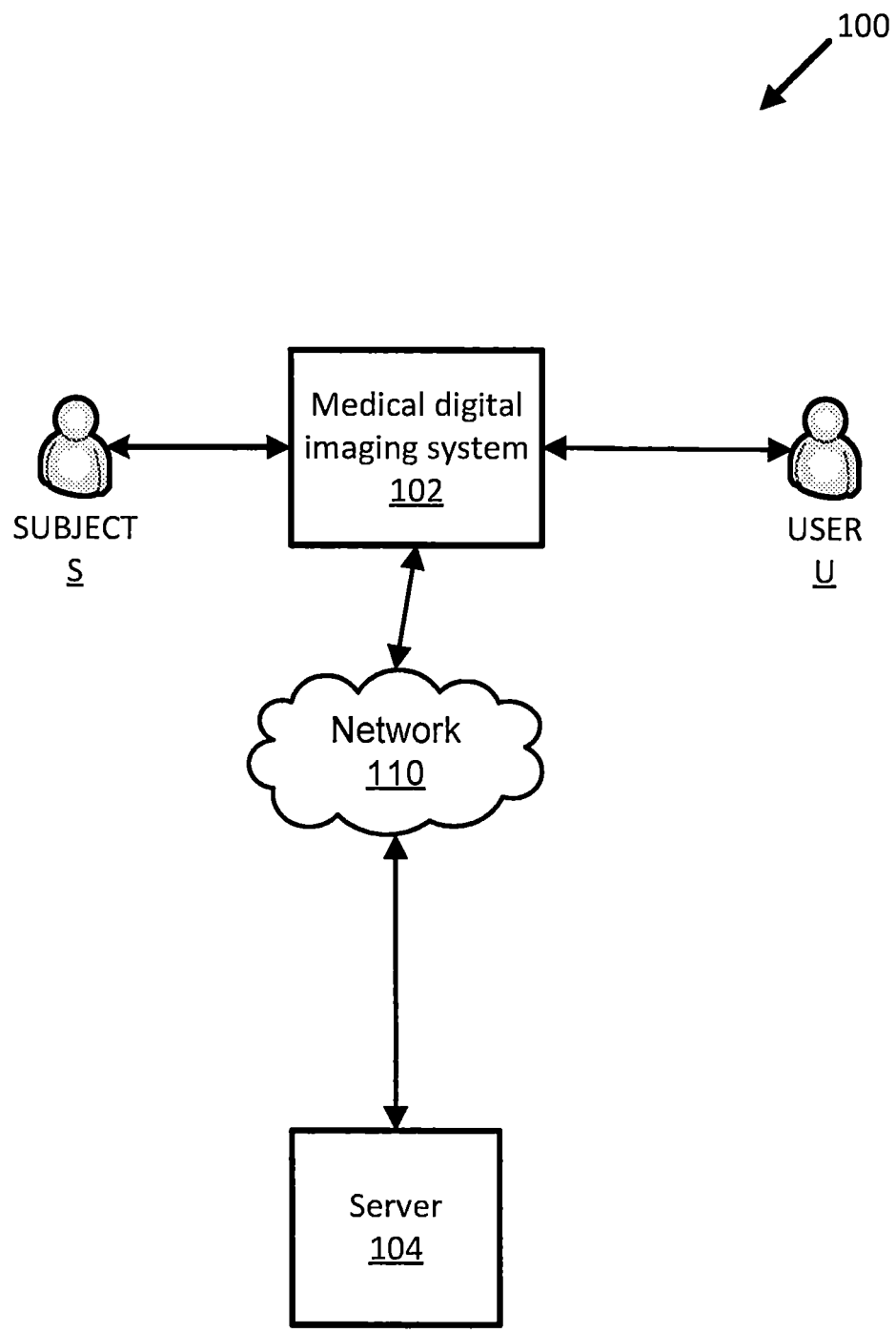
FIG. 1 is a schematic view of an example medical imaging environment.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

Broadly, the present disclosure is directed to medical digital imaging. Certain types of medical digital imaging identify and/or track pupil movement. Systems and methods of this disclosure are directed towards pupil identification during medical digital imaging.

In particular, systems and methods disclosed herein involve detecting a pupil edge in a digital image. A "pupil edge," as used herein, is meant to include a boundary between the pupil and an iris. Detecting pupil edges finds application in, for example, photorefraction ocular screening and digital fundus imaging, particularly when triggered by eye tracking. Photorefraction ocular screening devices can determine refractive error by determining a slope of an intensity distribution of pixels across a pupil. The slope of the intensity distribution can be used to infer spherical error of a test subject's eye.

Slope determination typically relies on an accurate detection of the pupil edge. Accurate determination of a pupil size is needed to infer a subject's spherical error from a calculated slope of a pixel intensity distribution. Additionally, intensity distributions at the pupil edges decrease gradually and should be excluded when calculating a slope profile of the intensity distribution across the pupil.

Existing edge detection techniques are not specific to pupil edge detection. One example edge detection technique is the Canny edge detection algorithm. Typically, existing edge detection techniques are based on a gradient function or intensity histogram for calculating threshold values that can then be used for determining pixels that represent an edge of an object within an image.

Such techniques have many drawbacks for pupil edge detection. For instance, the Canny edge detection algorithm is processing intensive. An example advantage of the systems and methods contemplated herein is improved processing efficiency for pupil edge detection. Improving the processing efficiency thereby reduces processing requirements and/or speeds up processing.

Quickly processing pupil images is particularly valuable in the context of ocular refractive error correction and/or fundus imaging including pupil tracking. Typically, imaging devices capture many frames of the pupil or fundus within a short duration. For instance, during example ocular refractive error testing disclosed in U.S. Pat. No. 9,402,538, "Photorefraction ocular screening device and methods," hereby incorporated by reference in its entirety, a total of twenty-three frames are captured and processed in seconds. For eye tracking, pupil identification is typically needed within milliseconds to capture fundus images before the subject's gaze changes.

Another example advantage of the systems and methods contemplated herein is improved accuracy of estimated pupil size and detection. Existing techniques can inaccurately determine pupil size. It has been observed that Canny edge detection techniques incorrectly estimate pupil size by 0.2 mm or even by 0.5 mm. In some instances, existing pupil edge detection techniques fail to find a pupil-iris threshold, particularly on medium or small pupils.

Generally, systems and methods contemplated herein exclude various human and pathologic factors from affecting determination of pupil edge pixel thresholds. Existing techniques, such as gradient and histogram methodologies, usually include such factors, which can explain their inaccuracy or even inability to determine pupil edges. Example factors include images where the pupil is partially obscured or includes: eye lids, eye lashes, and cataracts.

FIG. 1 shows example medical imaging environment 100. Example medical imaging environment 100 includes medical digital imaging system 102, subject S, and user U. In some implementations, medical digital imaging system 102 is in communication with server 104, typically via network 110. User U uses medical digital imaging system 102 to obtain one or more images of subject S. Other embodiments can include more or fewer components.

In some implementations, medical imaging environment 100 is in a traditional medical environment, such as a general practice facility, an urgent care facility, a hospital, and the like. Alternatively, medical imaging environment 100 is a non-traditional medical environment, such as a school. In some instances, user U is not formally medically trained.

Medical digital imaging system 102 obtains and processes one or more digital images of an ocular fundus or pupil of subject S. Medical digital imaging system 102 can be used to assist user U when screening for, monitoring, or diagnosing various eye conditions or diseases. Example eye conditions and diseases include refractive error, hypertension, diabetic retinopathy, glaucoma and papilledema. It will be appreciated that user U operating medical digital imaging system 102 can be different from a person evaluating the resulting images. For example, medical digital imaging system 102 transmits one or more images or results to server 104. Then, a clinician different from user U can access server 104 to then analyze the results or images.

Medical digital imaging system 102 can have different sizes depending on the particular implementation. For example, medical digital imaging system 102 can be portable and sized such that it can be hand held. Portable, hand held sizing can be advantageous for off-site screening of a particular population, such as school children or nursing home occupants. In other implementations, medical digital imaging system 102 is configured for more stationary operations, such as within a medical facility.

In some implementations, medical digital imaging system 102 provides relatively immediate screening of subject S. Example screening can include capturing one or more images, displaying stimuli to subject S, capturing images of subject S's reaction to the stimuli, and an analysis of images including the subject's reaction. Based on this processing, medical digital imaging system 102 can display one or more different results reflecting analysis of the images.

Medical digital imaging system 102, in some implementations, displays stimuli and captures images of the subject's ocular fundus or pupils. In turn, medical digital imaging system 102 transmits those images for later viewing and analysis by trained clinicians or digital image processing algorithms.

Medical digital imaging system 102 is particularly configured to capture digital images including a pupil of subject S and to identify edge pixels of the pupil. Subsequently, medical digital imaging system 102 can use the identified pupil edge in various ways. For instance, determining pupil edges aids in identifying pupil location and movement during refractive error screening. As another example, identifying a pupil edge can be used as part of eye tracking, where the eye tracking can be used to initiate image capture of an ocular fundus. Other uses of determining pupil edges in digital image are contemplated.

One technique for fundus imaging requires mydriasis, dilation of a subject's pupil, which can be painful and/or inconvenient to the subject S. Example medical digital imaging system 102 can be used in mydriatic or non-mydriatic conditions. That is, medical digital imaging system 102 can capture images without requiring a mydriatic drug to be administered to the subject S before imaging.

In terms of pupil dilation, medical digital imaging system 102 can capture images with pupil sizes smaller than 4.5 mm. In some instances, medical digital imaging system 102 can capture wide FOV images with pupil sizes no greater than 3.5 mm or even no greater than 2.5 mm. Of course, medical digital imaging system 102 can capture images with larger pupil sizes, such as those greater than 5 mm.

Medical digital imaging system 102 includes a housing that supports system components. For instance, the housing supports one or two apertures for imaging one or two eyes at a time. In some embodiments, the housing supports positional guides for the subject S, such as an adjustable chin rest. The positional guides help align the subject's eyes with the apertures. In some embodiments, the apertures are adjustable to align them with the subject's eyes. Once the subject's eyes are aligned, user U can initiate image capture sequencing.

Medical digital imaging system 102 is typically connected to network 110. Network 110 can include any type of wireless network, a wired network, or any communication network known in the art. For example, wireless connections can include cellular network connections and connections made using protocols such as 802.11a, b, and/or g. In other examples, a wireless connection can be accomplished directly between medical digital imaging system 102 and an external display using one or more wired or wireless protocols, such as Bluetooth, Wi-Fi Direct, radio-frequency identification (RFID), or Zigbee. Other configurations are possible.

Server 104 communicates with medical digital imaging system 102 and additional devices. For example, server 104 receives fundus images from medical digital imaging system 102 and stores the images, and possible accompanying data such as patient data, in one or more databases. Clinicians can then access stored images for analysis. Server 104 includes one or more components of computing device 801 shown in FIG. 12, described in more detail below.

Figure 2:
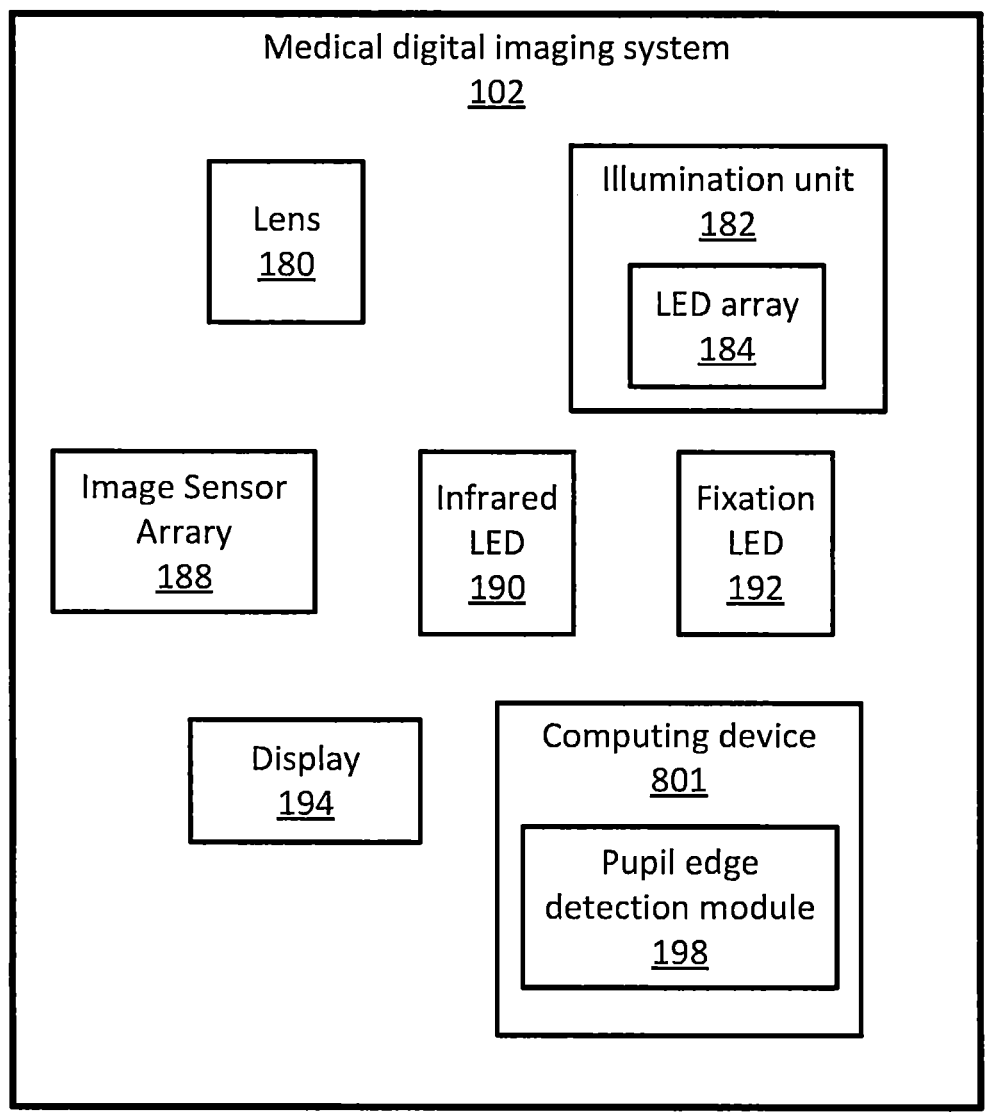
FIG. 2 is a schematic diagram showing example components of the medical digital imaging system used in the environment of FIG. 1.

FIG. 2 is a schematic diagram showing example components of medical digital imaging system 102. Medical digital imaging system 102 includes lens 180, illumination unit 182, image sensor array 188, infrared LED 190, fixation LED 192, display 194, and computing device 801. Each component is in communication with, at least, computing device 801. Additional components of medical digital imaging system 102, not shown in FIG. 2, can include a speaker unit, a range finder unit, and a front window. Commercial embodiments of medical digital imaging system 102 include the Welch Allyn RetinaVue™ 100 Imager and the Welch Allyn Spot™ Vision Screener (Welch Allyn, Skaneateles Falls, N.Y.). Other embodiments can include more or fewer components.

Lens 180 focuses light onto image sensor array 188. Typically, lens 180 is adjustable. For example, lens 180 can be implemented as a variable focus liquid lens or a mechanically adjustable lens. A liquid lens is an optical lens whose focal length can be controlled by the application of an external force, such as a voltage. The lens includes a transparent fluid, such as water or water and oil, sealed within a cell and a transparent membrane. By applying a force to the fluid, the curvature of the fluid changes, thereby changing the focal length. This effect is known as electrowetting. A mechanically adjustable lens can change a focal length of the lens using, for example, by a stepping motor, a voice coil actuator, an ultrasonic motor, or a piezoelectric actuator.

Illumination unit 182 is an optional component and illuminates the eye fundus during certain image capture operations. Illumination unit 182 is configured to illuminate the eye fundus of the subject. Illumination of illumination unit 182 is coordinated with operation of image sensor array 188.

As shown, illumination unit 182 includes LED array 184. In other embodiments, illumination unit 182 can include one or more additional lighting units. In addition, lighting elements in illumination unit 182 can include non-light-emitting diode components. LED array 184 can be single color or multi-color. For example, LED array 184 is a three-channel RGB LED, where each die is capable of independent and tandem operation.

Image sensor array 188 receives and processes light reflected off of the subject. Image sensor array 188 can be a complementary metal-oxide semiconductor (CMOS) sensor array or a charge coupled device (CCD) sensor. Image sensor array 188 has a plurality of rows of pixels and a plurality of columns of pixels. For example, in various implementations, the image sensor array has about 1280 by 1024 pixels, about 640 by 480 pixels, about 1500 by 1152 pixels, about 2048 by 1536 pixels, or about 2560 by 1920 pixels. Other pixel sizes are possible.

Pixels in image sensor array 188 include photodiodes that have a light-receiving surface and have substantially uniform length and width. During exposure, the photodiodes convert the incident light to a charge. Exposure and readout of image sensor array 188 can be performed as rolling shutter or global shutter.

In rolling shutter exposure and readout, each row of pixels is exposed for the same time duration, however, each row of pixels is exposed at different points in time. Rolling shutter exposure begins at a top row of image sensor array 188 and each row below is successively exposed and then readout. Typically, exposure of the row below begins before completing exposure and readout of the row above. In this way, at any given time during image sensor array 188 exposure, more than one row of pixels are exposed.

In global shutter exposure, all of the photodiodes in image sensor array 188 are exposed simultaneously and for the same length of time. Then readout is performed for each photodiode. Because all photodiodes are subjected to readout at the same time, usually the image sensor array must wait until readout is completed before beginning the next frame's exposure. Thus, global shutter operations typically have slower frame rates than rolling shutter operations.

Infrared LED 190 illuminates the eye fundus with near-infrared light. Infrared light emitted by infrared LED 190 preferably has a central wavelength of 850 nanometers. In some instances, infrared LED 190 emits infrared light during a preview and/or eye tracking mode. Alternatively, infrared LED 190 emits infrared light during image capture operations part of the ocular examination.

Medical digital imaging system 102 optionally includes fixation LED 192. Fixation LED 192 produces light to guide the subject's eye for alignment. Fixation LED 192 can be a single color or multicolor LED. For example, the fixation LED 192 can produce a beam of green light that appears as a green dot when subject S looks into the medical digital imaging system 102. Other colors and designs, such as a cross, "x" and circle are possible.

Medical digital imaging system 102 can also include display 194. Display 194 shows images and/or results produced by medical digital imaging system 102. In the example embodiment, a housing supports display 194. In other embodiments, display 194 connects to the image processor through wired or wireless connection, and can be instantiated as a smart phone, tablet computer, or external monitor.

Medical digital imaging system 102 also includes computing device 801, which typically includes a processing unit and a computer readable storage device. In some embodiments, the computer-readable storage device stores data instructions, which when executed by the processing device, causes the processing device to perform one or more of the functions, methods, or operations, described herein. For example, computing device 801 includes pupil edge detection module 198. Pupil edge detection module 198 is configured to perform the functions and operations described herein. An example computing device 801 is illustrated and discussed in more detail with reference to FIG. 12.

Figure 3:
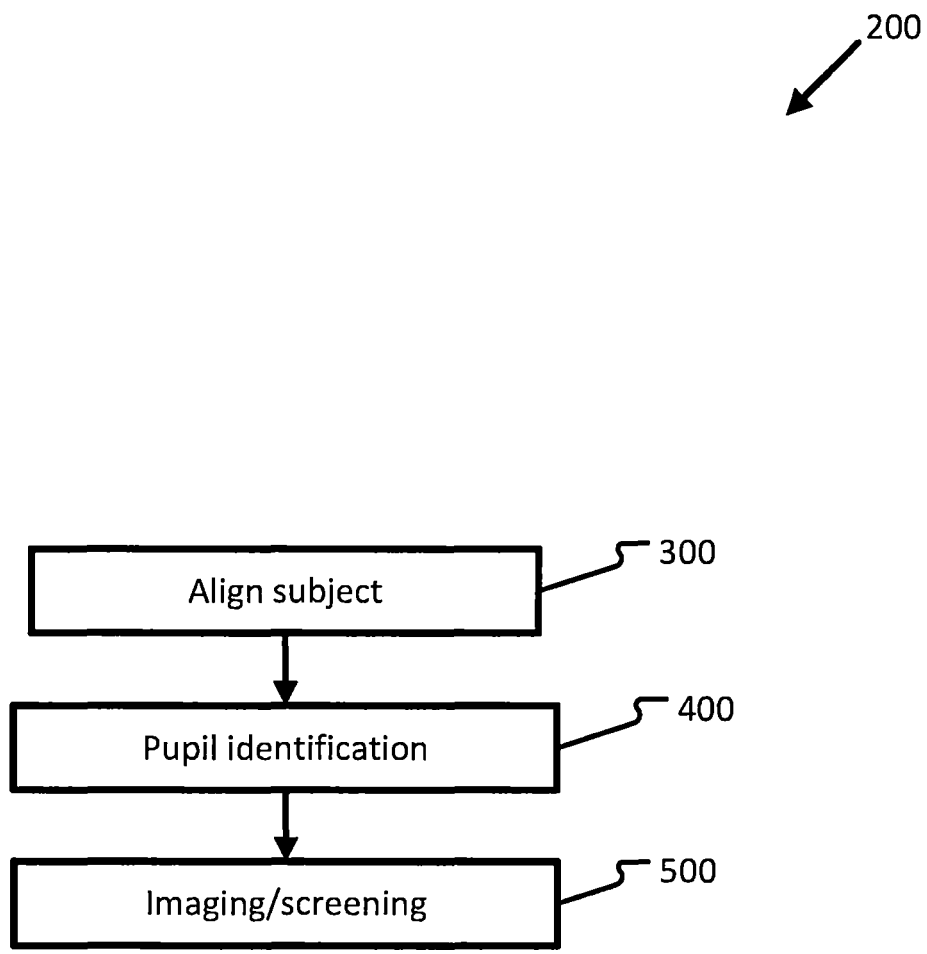
FIG. 3 shows an example method of imaging a subject using the example medical imaging environment of FIG. 1.

FIG. 3 illustrates example method 200 for imaging a subject. Example method 200 includes aligning a subject (operation 300), pupil identification (operation 400), and imaging/screening (operation 500). Example method 200 is typically performed using medical digital imaging system 102 described above. Example method 200 can be performed without administering mydriatic substances to the subject and, accordingly, a subject's pupil dilation is usually no greater than 5 mm. Other embodiments can include more or fewer operations.

Example method 200 begins by aligning a subject (operation 300). Aligning a subject (operation 300) can include adjusting a relative spacing between the subject and the medical digital imaging system. In some implementations, the subject is seated in a chair during examination. Alternatively, the subject may be aligned using one or more features on the medical digital imaging system, such a chin rest. In some instances, a user holds a hand-held version of medical digital imaging system and can move closer or further away from the subject while the subject is sitting or standing. Alignment of the subject and medical digital imaging system can be guided by on-screen displays that can instruct the user to move in one or more directions. Range finding units can guide this alignment.

After the subject is aligned (operation 300), pupil identification (operation 400) commences. Generally, pupil identification includes identifying one or more pupils of the subject in one or more digital images. Operations performed during pupil identification (operation 400) are described in greater detail below.

Then, imaging and/or screening (operation 500) operations are performed. In some instances, one or more images of the subject's ocular fundus are captured and subsequently analyzed. Alternatively, the subject undergoes ocular refraction screening. During either, or both, operations, one or more visual stimuli are displayed by the medical digital imaging system. In some instances, the medical digital imaging system displays one or more results of the imaging or ocular screening.

Figure 4:
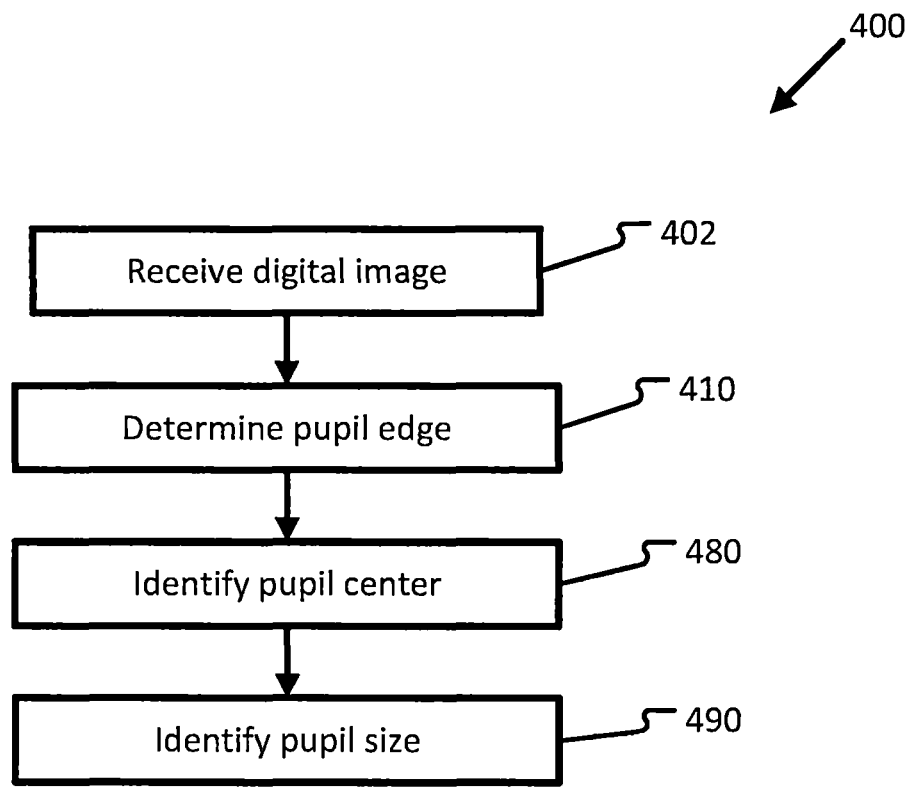
FIG. 4 shows example operations performed during the pupil identification operation of FIG. 3.

FIG. 4 illustrates example operations performed during pupil identification (operation 400). As shown, pupil identification (operation 400) includes receiving a digital image (operation 402), determining a pupil edge (operation 410), identifying a pupil center (operation 480), and identifying pupil size (operation 490).

Pupil identification (operation 400) typically begins by receiving a digital image (operation 402). Digital images received during operation 402 are captured by the image sensor array in the medical digital imaging system. These images are usually captured during near infrared light illumination. In some instances, one or more digital images are received from an external apparatus or retrieved from remote storage.

After receiving one or more digital images (operation 402), a pupil edge is determined (operation 410). Broadly, determining a pupil edge (operation 410) includes operations resulting in generation of an image showing the pupil outline. Additional details regarding determining a pupil edge (operation 410) are described below with reference to, at least, FIGS. 5-9.

A pupil center and pupil size (operations 480 and 490) can be determined upon determining the pupil edge (operation 410). Generally, identifying pupil center and pupil size (operations 480 and 490) are used during ocular refractive error determinations and/or eye tracking operations.

Figure 5:
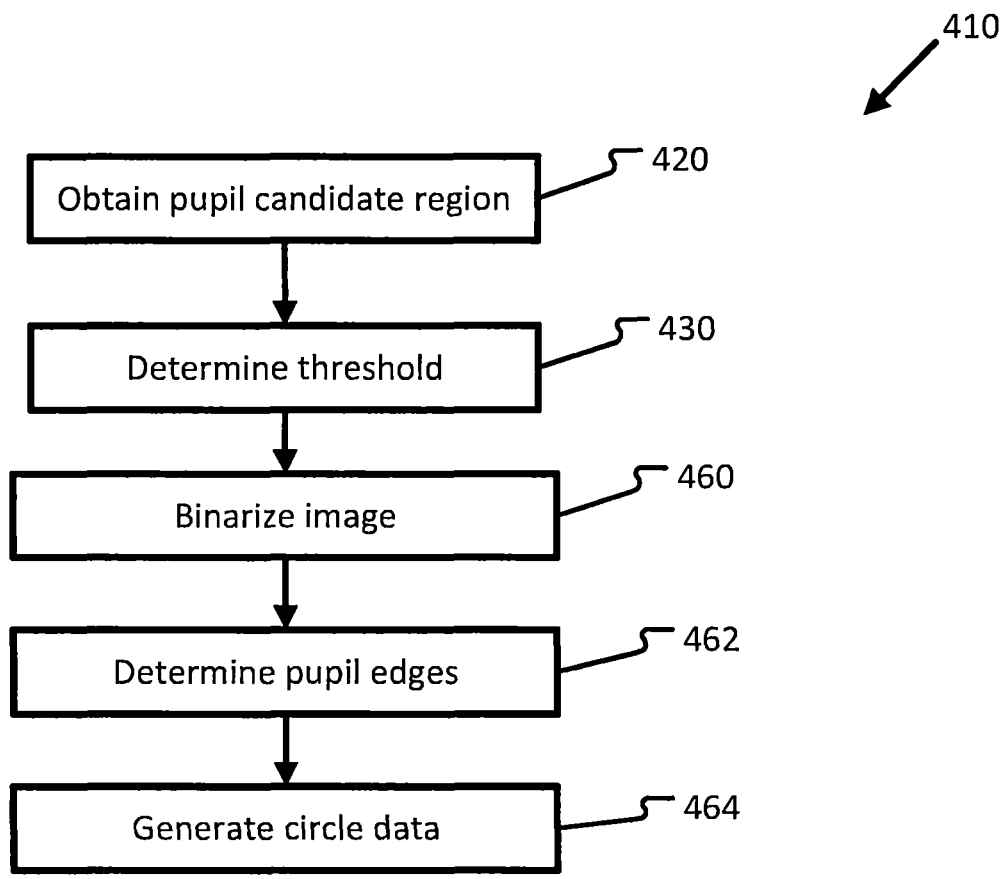
FIG. 5 shows example operations performed during the pupil edge determination operation of FIG. 4.

FIG. 5 shows example operations performed during pupil edge determination (operation 410). Typically, pupil edge determination (operation 410) includes obtaining a pupil candidate region (operation 420), determining a threshold (operation 430), binarizing an image (operation 460), determining pupil edges (operation 462), and generating circle data (operation 464).

After receiving a digital image (operation 402), a pupil candidate region is obtained (operation 420). One or more previous processes have determined that the pupil candidate region includes the pupil of a test subject. Determining a pupil candidate region is described in detail in U.S. Pat. No. 9,402,538.

The pupil candidate region is square or rectangular shaped. Typically, the pupil candidate region is square and has side lengths between 70 and 80 pixels. The pupil candidate region is usually larger than 65 pixels by 65 pixels to provide additional space between the pupil edges and the edge areas of the pupil candidate region. In some implementations, the pupil candidate region is 11.5 mm by 11.5 mm. In other implementations, the pupil candidate region is 71 pixels by 71 pixels. Other sizes of pupil candidate region are contemplated.

Figure 6:
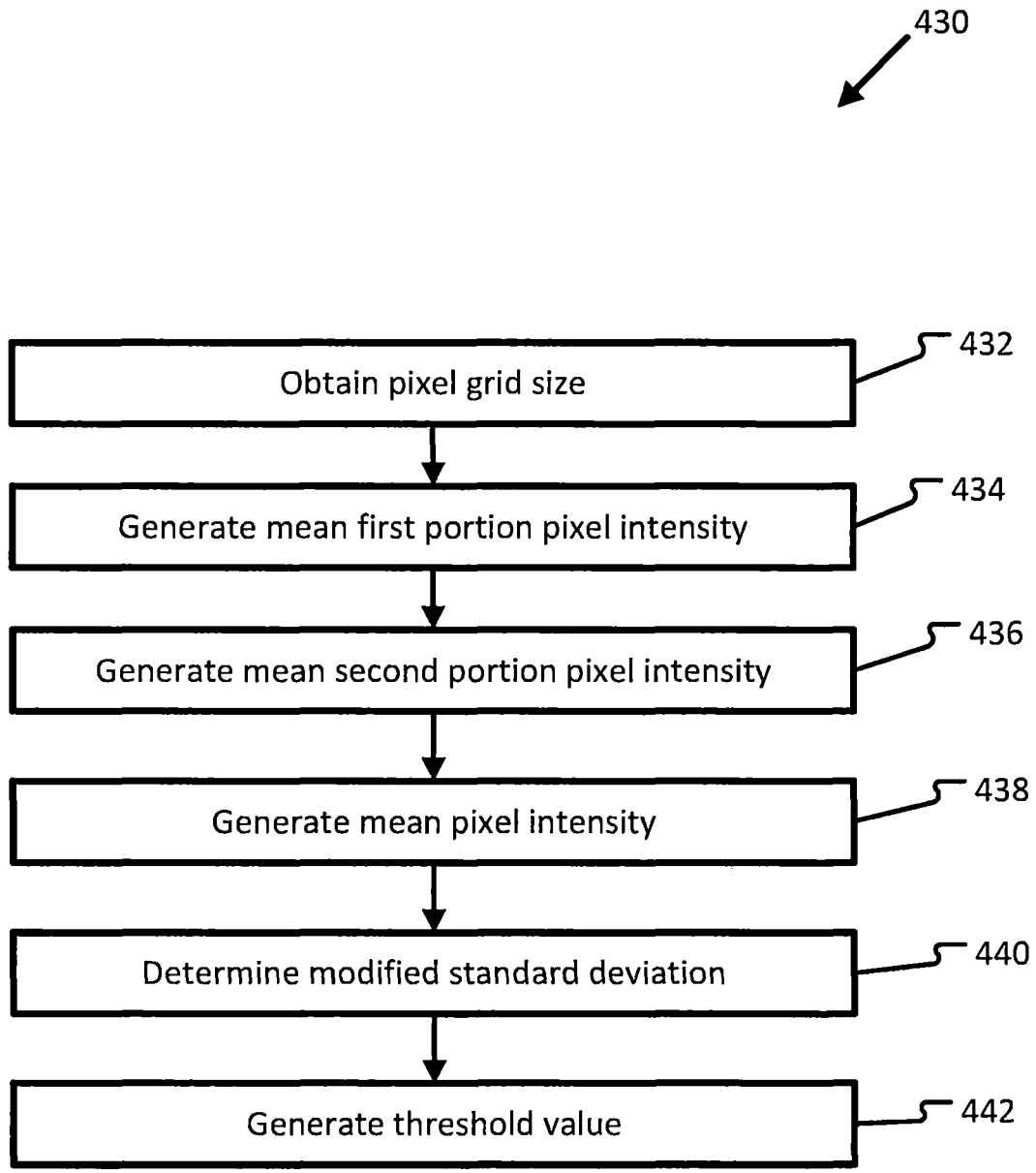
FIG. 6 shows example operations performed during the determining a threshold operation of FIG. 5.

After obtaining a pupil candidate region (operation 420), a threshold is determined (operation 430). FIG. 6 shows determining a threshold (operation 430) in greater detail. As shown, determining a threshold includes obtaining a pixel grid size (operation 432), generating a mean first portion pixel intensity (operation 434), generating a mean second portion pixel intensity (operation 436), generating a mean pixel intensity (operation 438), determining a modified standard deviation (operation 440), and generating a threshold value (operation 442).

Generating a threshold (operation 430) begins by obtaining a pixel grid size (operation 432). Generally, the pixel grid is a region of interest that is evaluated during operation 430. In operation 430, two areas of the pupil candidate region are evaluated and the size and shape of those two areas are defined by the pixel grid. Usually, each region of interest has the same pixel grid size.

Regarding the location of the pixel grids within the pupil candidate region, each pixel grid is preferably positioned such that pupil and non-pupil objects are unlikely to be included. Example non-pupil objects include eye lids and eye lashes. Usually, the pixel grids are positioned along the left and right side edges of the pupil candidate region. In some instances, the pixel grids are centered along the left and right side edges of the pupil candidate region. Usually, the pixel grids are not positioned along the top or bottom edges of the pupil candidate region.

The pixel grid can be different polygonal shapes, but typically the pixel grid is rectangular. The pixel grid is usually sized such that it extends along an edge much more than it extends into the pupil candidate region towards the pupil. An example pixel grid size is 2 columns by 31 rows. Another example pixel grid size is 3 columns by 22 rows. Yet another example pixel grid size is 4 columns by 20 rows. Other pixel grid sizes are contemplated.

Obtaining the pixel grid size (operation 432) can include determining a pixel grid size based on one or more factors, such as a size of the pupil candidate region. In some instances, the pixel grid size is predetermined and obtaining the pixel grid size (operation 432) includes retrieving a saved or predetermined pixel grid size.

Figure 7:
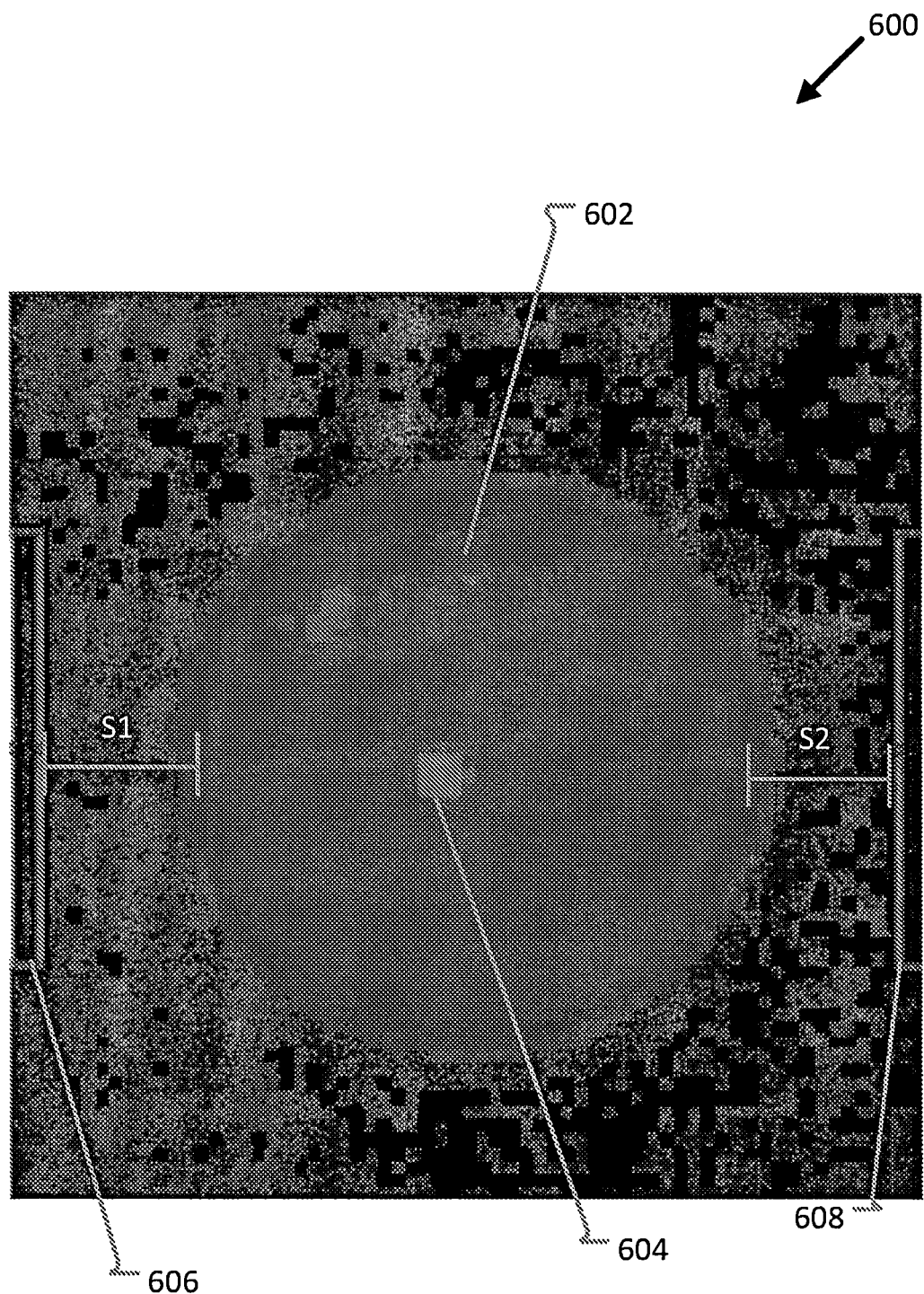
FIG. 7 shows an example pupil candidate region.

Referring to FIG. 7, an example pupil candidate region 600 is shown. Pupil candidate region 600 includes pupil 602, glint area 604, pixel grid 606 and pixel grid 608. Pupil candidate region 600 is 71 pixels by 71 pixels.

Pixel grid 606 is positioned along the left edge of pupil candidate region 600 and vertically centered. Pixel grid 606 and pupil candidate region 600 are sized such that there is spacing S1 between pixel grid 606 and pupil 602. Pixel grid 608 is positioned along the right edge of pupil candidate region 600 and vertically centered. Pixel grid 608 and pupil candidate region 600 are sized such that there is spacing S2 between pixel grid 608 and pupil 602. When S1 and S2 are nonzero, there is a low likelihood that pixel grids 606 and 608 include artifacts or the pupil, which can negatively impact the subsequent determinations in operation 430.

Pixel grid 606 and pixel grid 608 are similarly sized: 2 columns by 31 rows. Taking the upper left corner of pupil candidate region 600 as coordinate (0,0), coordinates for pixel grid 606 corners are: (0,17), (1,17), (0,47), and (1,47). Pixel grid 608 is positioned along the right edge of pupil candidate region 600 and vertically centered. Coordinates for pixel grid 608 corners are: (70,17), (71,17), (70,47), and (71,47).

In another implementation, coordinates for pixel grid 606 corners are: (0,20), (1,20), (0,50), and (1,50). Pixel grid 608 is positioned along the right edge of pupil candidate region 600. Coordinates for pixel grid 608 corners are: (69,20), (70,20), (69,50), and (70,50).

Referring again to FIG. 6, after obtaining a pixel grid size (operation 432), a mean first portion pixel intensity is generated (operation 434). Generating the mean first portion pixel intensity (operation 434) includes evaluating a first portion of the pupil candidate region 600. The first portion of the pupil candidate region is defined by the pixel grid. The first portion can be either the first pixel grid (e.g., pixel grid 606 in FIG. 7) or the second pixel grid (e.g., pixel grid 608 in FIG. 7); order is not important.

Generating the mean first portion pixel intensity (operation 434) includes determining a pixel intensity for each pixel in the first portion. For example, in a pixel grid size of 2 columns by 31 rows, an intensity value is determined for each of the 62 pixels in the first portion. The intensity value can be on a variety of scales, such as 0-256, 0-1000, etc.

Next, a summed first portion pixel intensity is determined by summing the pixel intensity for each pixel in the first portion. Then a first portion mean pixel intensity is determined by dividing the summed first portion pixel intensity by the number of pixels in the first portion. These operations can be shown as calculating the mean in equation (1), where Xi is the pixel intensity of each pixel and the first portion includes n pixels:

$$\text{First Portion Mean Pixel Intensity} = \frac{1}{n} * \sum_{i=1}^{n} Xi \qquad (1)$$

A mean second portion pixel intensity is determined (operation 436) by evaluating a second portion of the pupil candidate region 600. The second portion of the pupil candidate region is defined by the pixel grid. The second portion is the opposite portion from the first portion evaluated during operation 434.

Generating the mean second portion pixel intensity (operation 436) includes determining a pixel intensity for each pixel in the second portion. The intensity value is on the same scale as that used for the first portion, for consistency.

Next, a summed second portion pixel intensity is determined by summing the pixel intensity for each pixel in the second portion. Then a second portion mean pixel intensity is determined by dividing the summed second portion pixel intensity by the number of pixels in the second portion. These operations can be shown as calculating the mean in equation (2), where Yi is the pixel intensity of each pixel and the second portion includes n pixels:

$$\text{Second Portion Mean Pixel Intensity} = \frac{1}{n} * \sum_{i=1}^{n} Yi \qquad (2)$$

After generating a mean first portion pixel intensity (operation 434) and generating a mean second portion pixel intensity (operation 436), a mean pixel intensity is generated (operation 438). The mean pixel intensity is generated (operation 438) by summing the mean first portion pixel intensity and the mean second portion pixel intensity, and dividing that sum by 2.

As an alternative to operations 434, 436, and 438, a mean pixel intensity is generated by treating the first portion pixels and the second portion pixels as a single data set. Then, the mean pixel intensity is generated by determining the mean of the pixel intensity for each pixel in the first portion and the second portion.

Next, a modified standard deviation is determined (operation 440). The modified standard deviation is generated (operation 440) by first calculating a standard deviation of each pixel intensity for each pixel in both the first portion and the second portion (i.e., treating the first portion and second portion as a single data set).

After calculating the standard deviation of the pixel intensity for each pixel within the first portion and the second portion, the modified standard deviation is determined (operation 440) by multiplying the standard deviation by a multiplier. Typically, the multiplier is a number greater than 1 but no greater than 3. In some implementations, the multiplier is 2.

Then a threshold value is generated (operation 442). The threshold value is generated (operation 442) by summing the mean pixel intensity and the modified standard deviation.

Referring again to FIG. 5, after determining the threshold, the image is binarized (operation 460). Broadly, binarizing the image involves converting the digital pupil image into an image or grid where each pixel has one of two values, typically a 0 or a 1. The resulting image or grid is a representation of the pupil in the digital pupil image.

Typically, the digital pupil image pixels have one or more values. For example, if the digital pupil image is in black and white, each pixel has one value, typically on a scale of 0-255. In some instances, this value can be the same as a pixel intensity value. If the digital pupil image in color, each pixel can have three values (one red value, one green value, and one blue value), where each value is typically on a scale of 0-255. In some implementations, an intensity value has been determined for each pixel.

Binarizing the image (operation 460) includes evaluating a value of each pixel, such as the pixel intensity value, against the threshold value. If a pixel value is less than the threshold value, then that pixel is assigned a value corresponding to pixel intensities below the threshold, such as 0. If the pixel value is greater than the threshold value, then that pixel is assigned a value corresponding to pixel intensities above the threshold, such as 1. In an example implementation, with threshold value T, pixel values are assigned a value of 1 or 0 based on the following function:

$$g(x, y) = \begin{cases} 1 & \text{if } f(x, y) \geq T \\ 0 & \text{otherwise} \end{cases}$$

After binarizing the image (operation 460), pupil edges are determined (operation 462). Determining pupil edges can include generating a new image or grid, where the only nonzero pixels, or pixels with values, are those considered to be on the pupil edge. Various techniques are available to convert the binarized image to a pupil edge image.

For instance, determining pupil edges (operation 462) can include taking the leftmost and rightmost nonzero pixels in each row of the binarized image, and/or taking the topmost and bottommost nonzero pixels in each column of the binarized image, and assigning those pixels values of 1. The other pixels are assigned values of 0. Other implementations are possible.

After pupil edges are determined (operation 462), circle data are generated (operation 464). Circle data can include a center of the pupil, a pupil radius or diameter, and an image or grid showing circle data. In most implementations, pupil edge data generated during operation 462 are used during a best-fit circle determination. Results of the best-fit circle determination include a center of a circle, a circle radius, and a circle diameter. The circle represents the subject's pupil.

In some instances, portions of the pupil edge image are omitted from the best-fit circle generation (operation 464). These portions can sometimes include artifacts that may cause an inaccurate determination of the best-fit circle. In some implementations, a top portion of the pupil edge image is excluded from the best fit circle generation. For example, the top third (⅓) of the image is excluded. In some implementations, a bottom portion of the pupil edge image is excluded from the best fit circle generation. For example, the bottom quarter (¼) of the image is excluded. In some implementations, both a top portion and a bottom portion are excluded from the best fit circle.

Example 1—Artificial Eye Imaging

Figure 8A:
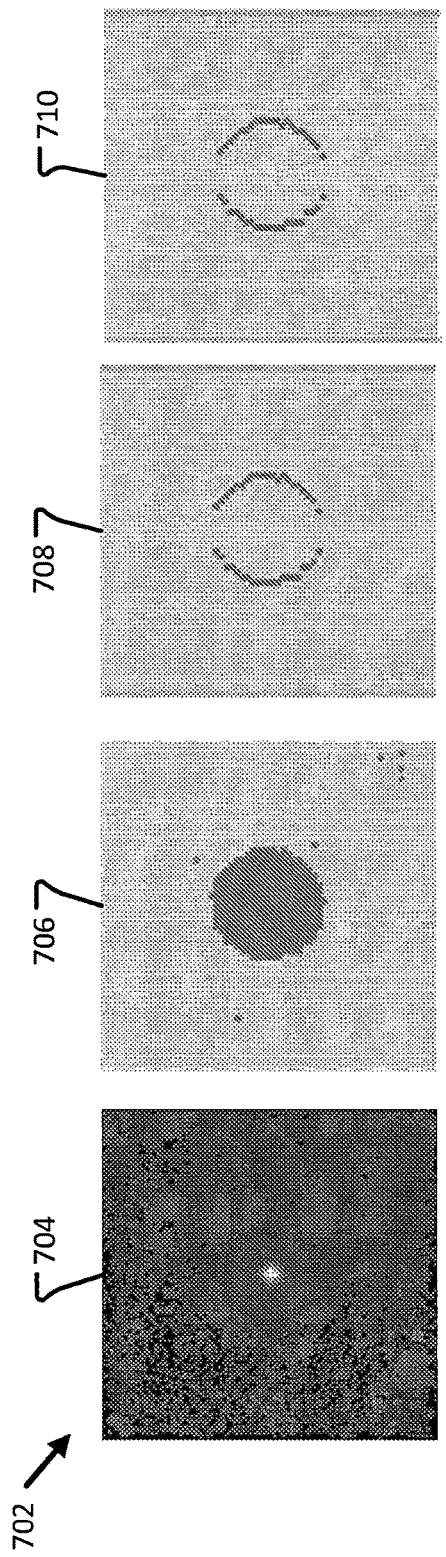
FIG. 8A shows exemplary image data generated during an implementation of the pupil identification operations shown in FIG. 4.

FIG. 8A shows exemplary image data 702 generated during example pupil identification method 400 described above. Data set 702 includes image data obtained while imaging a 3 mm artificial eye. Image 704 is the raw pupil data image. Image 704 is a 71 pixel by 71 pixel image and previous processing has determined that image 704 likely includes the subject's pupil.

Image 706 is a binarized image of image 704. Image 706 was generated using the threshold value determined during evaluation of image 704. Image 708 is a pupil edge image generated from binarized image 706. Image 710 is a limited circle data image generated by removing a top portion and a bottom portion from image 708. In this example, data from the top ⅓ of image 708 and data from the bottom ¼ of image 708 were removed to generate image 710. In a subsequent step, a best-fit circle is generated from data in image 710.

Figure 8B:
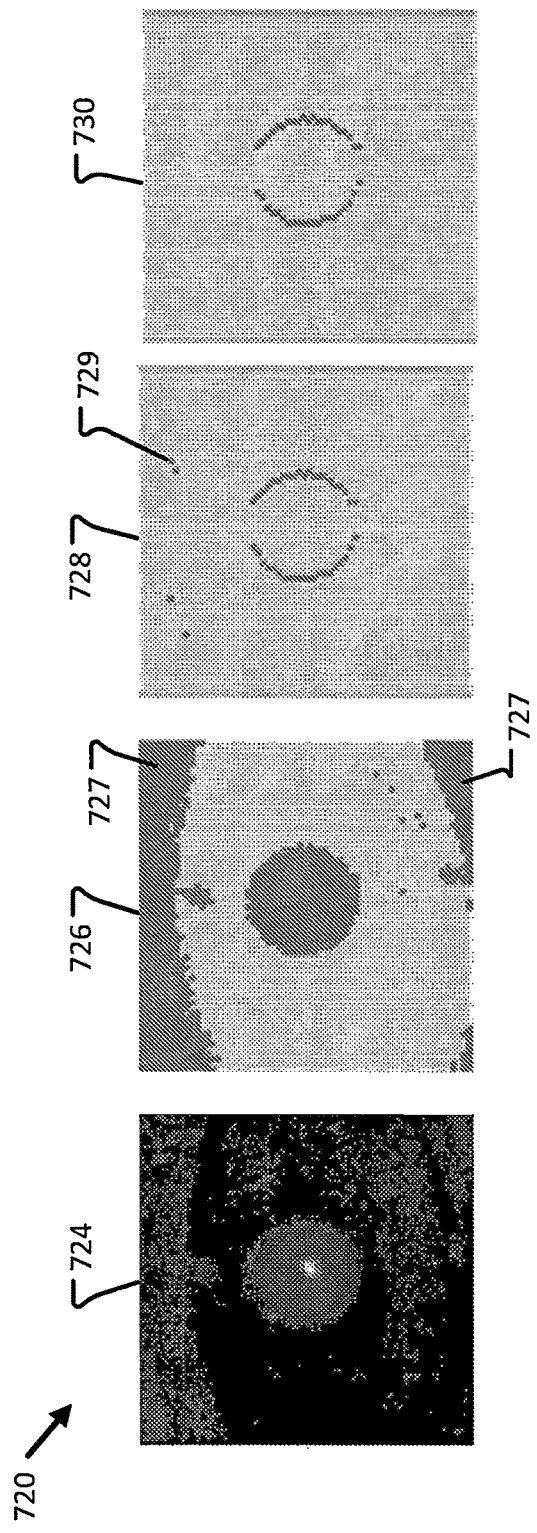
FIG. 8B shows exemplary image data generated during an implementation of the pupil identification operations shown in FIG. 4.

FIG. 8B shows exemplary image data 720 generated during example pupil identification method 400 described above. Data set 720 includes image data obtained while imaging a 3 mm artificial eye with an eye lid. Image 724 is the raw pupil data image. Image 724 is a 71 pixel by 71 pixel image and previous processing has determined that image 724 likely includes the subject's pupil.

Image 726 is a binarized image of image 724. Image 726 was generated using the threshold value determined during evaluation of image 724. As shown, image 726 includes eye lid artifacts 727.

Image 728 is a pupil edge image generated from binarized image 726. As shown, image 728 includes artifacts 729 resulting from pupil edge determination based on image 726. Artifacts 729 are not part of the pupil edge. Image 730 is a limited circle data image generated by removing a top portion and a bottom portion from image 728. In this example, data from the top ⅓ of image 728 and data from the bottom ¼ of image 728 were removed to generate image 730. By removing data from the top ⅓ of image 728, artifacts 729 will not be considered during best-fit circle generation based on image 730. In a subsequent step, a best-fit circle is generated from data in image 730.

Example 2—Human Occlusion and Opacity

Figure 9:
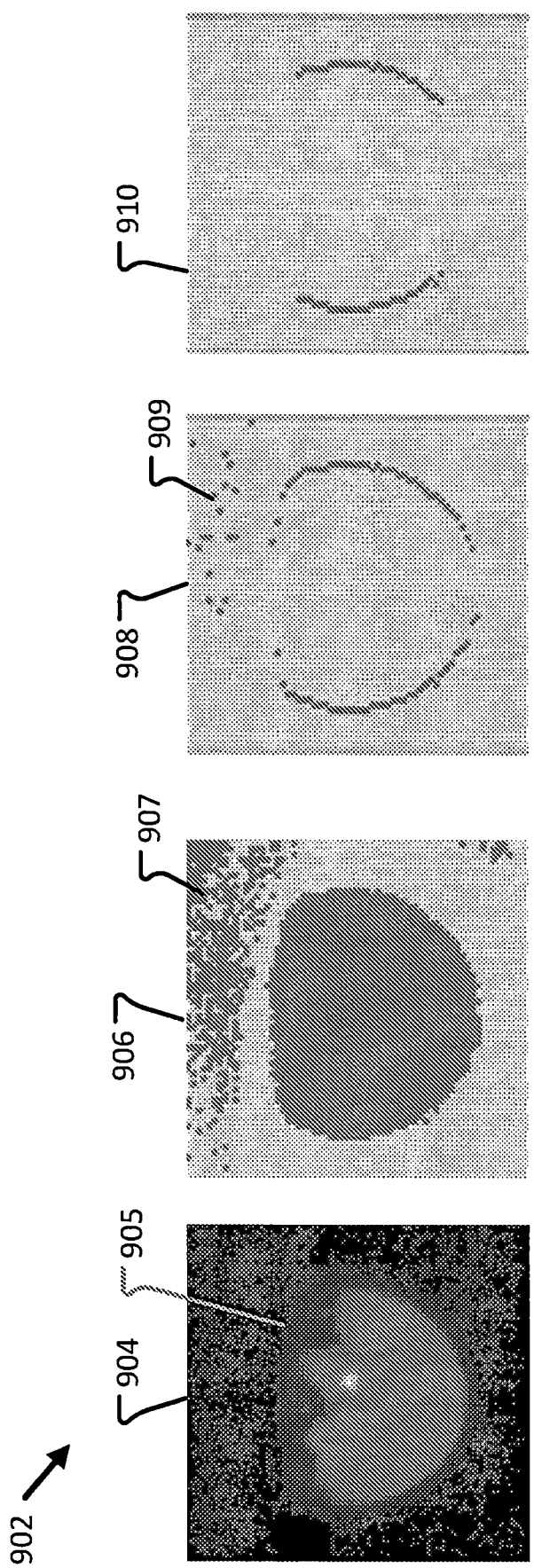
FIG. 9 shows exemplary image data generated during an implementation of the pupil identification operations shown in FIG. 4.
Figure 10:
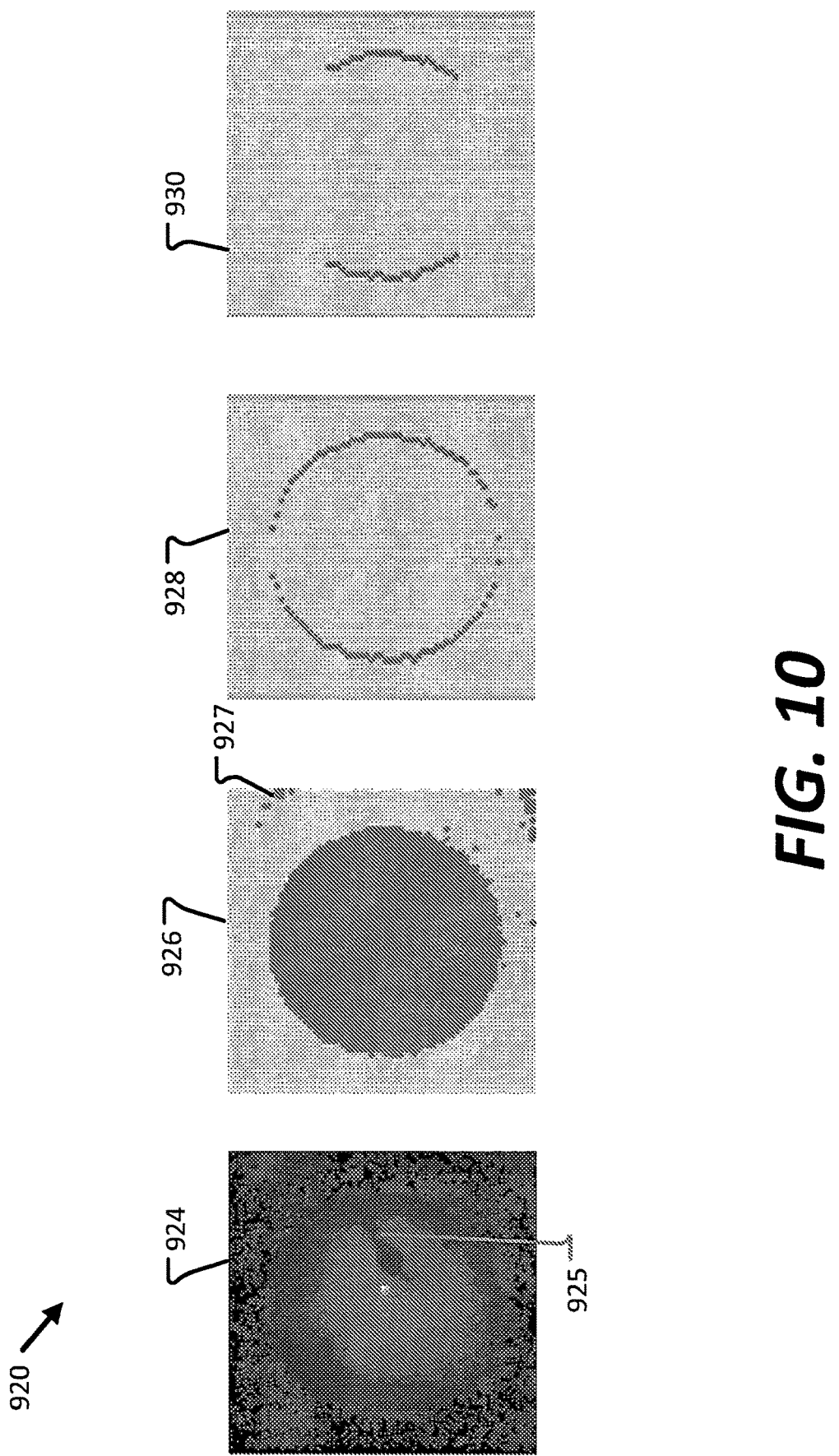
FIG. 10 shows exemplary image data generated during an implementation of the pupil identification operations shown in FIG. 4.
Figure 11:
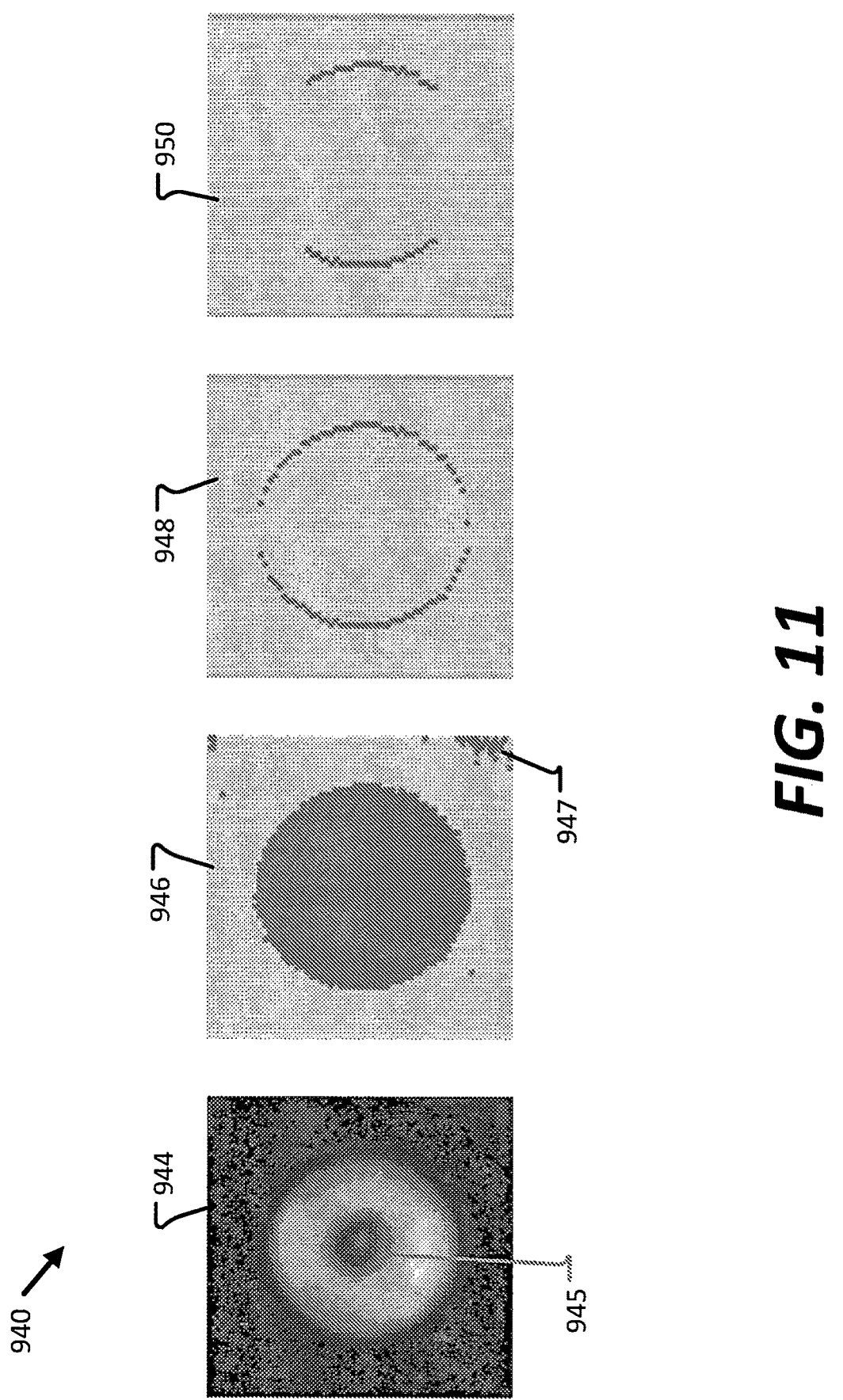
FIG. 11 shows exemplary image data generated during an implementation of the pupil identification operations shown in FIG. 4.

FIGS. 9-11 show example images generated from imaging a human eye. Each digital pupil image 904, 924, 944 includes one or more artifacts.

FIG. 9 shows exemplary image data 902 generated during example pupil identification method 400 described above. Image 904 is the raw pupil data image. As shown, eye lid and eye lash artifacts 905 are present in image 904. Image 904 is a 71 pixel by 71 pixel image and previous processing has determined that image 904 likely includes the subject's pupil.

Image 906 is a binarized image of image 904. Image 906 was generated using the threshold value determined during evaluation of image 904. As shown, image 906 includes eye lid/eye lash artifacts 907.

Image 908 is a pupil edge image generated from binarized image 906. As shown, image 908 includes artifacts 909 resulting from pupil edge determination based on image 906. Artifacts 909 are not part of the pupil edge. Image 910 is a limited circle data image generated by removing a top portion and a bottom portion from image 908. In this example, data from the top ⅓ of image 908 and data from the bottom ¼ of image 908 were removed to generate image 910. By removing data from the top ⅓ of image 910, artifacts 909 will not be considered during best-fit circle generation based on image 910. In a subsequent step, a best-fit circle is generated from data in image 910.

FIG. 10 shows exemplary image data 920 generated during example pupil identification method 400 described above. Image 924 is the raw pupil data image. As shown, cataract artifacts 925 are present in image 924. Image 924 is a 71 pixel by 71 pixel image and previous processing has determined that image 924 likely includes the subject's pupil.

Image 926 is a binarized image of image 924. Image 926 was generated using the threshold value determined during evaluation of image 924. As shown, image 926 includes artifacts 927.

Image 928 is a pupil edge image generated from binarized image 926. Image 930 is a limited circle data image generated by removing a top portion and a bottom portion from image 928. In this example, data from the top ⅓ of image 928 and data from the bottom ¼ of image 928 were removed to generate image 930. In a subsequent step, a best-fit circle is generated from data in image 930.

FIG. 11 shows exemplary image data 940 generated during example pupil identification method 400 described above. Image 944 is the raw pupil data image. As shown, cataract artifacts 945 are present in image 944. Image 944 is a 71 pixel by 71 pixel image and previous processing has determined that image 944 likely includes the subject's pupil.

Image 946 is a binarized image of image 944. Image 946 was generated using the threshold value determined during evaluation of image 944. As shown, image 946 includes artifacts 947.

Image 948 is a pupil edge image generated from binarized image 946. Image 950 is a limited circle data image generated by removing a top portion and a bottom portion from image 948. In this example, data from the top ⅓ of image 948 and data from the bottom ¼ of image 948 were removed to generate image 950. In a subsequent step, a best-fit circle is generated from data in image 950.

Figure 12:
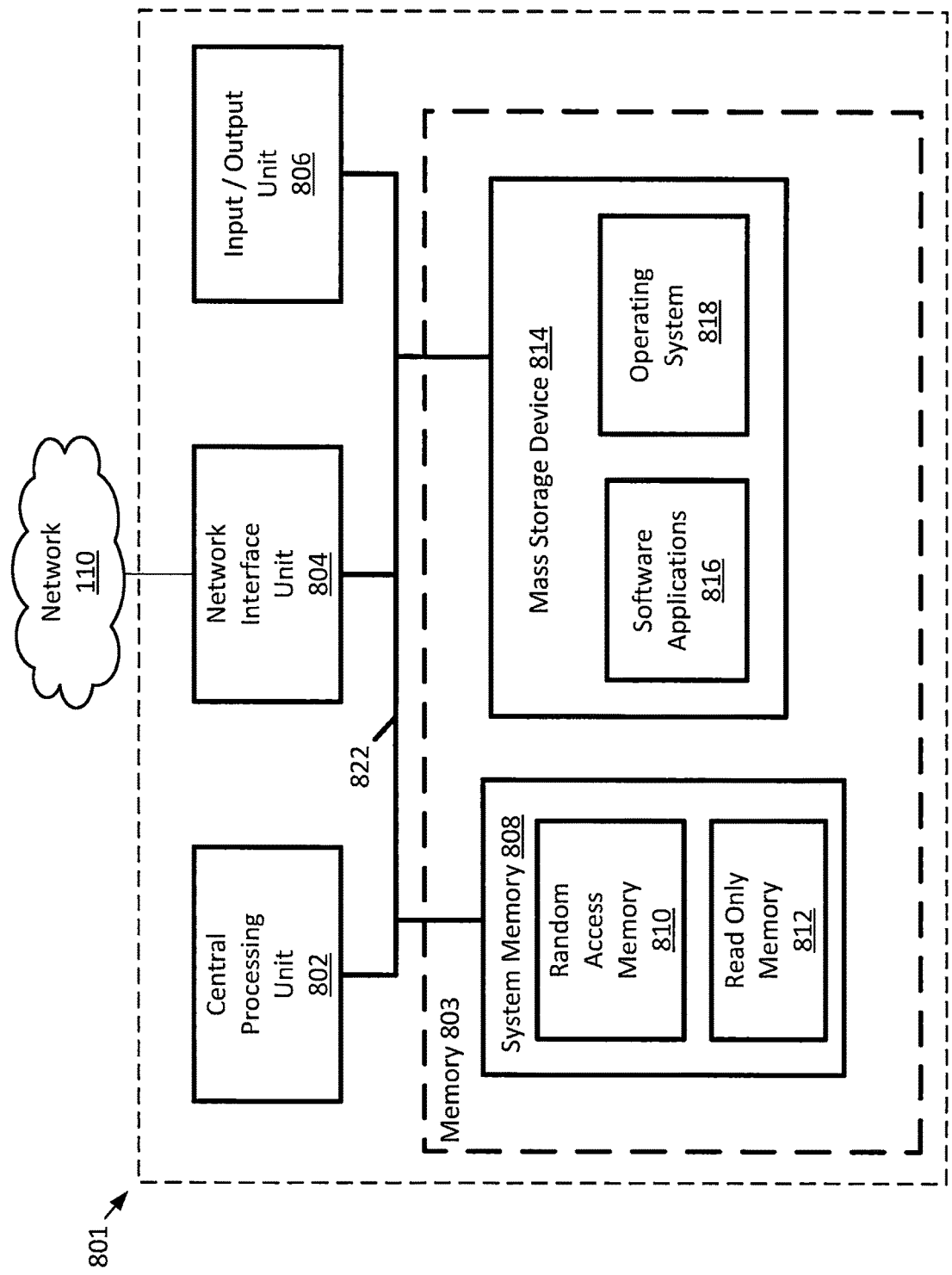
FIG. 12 shows example physical components of a computing device of the medical digital imaging system shown in FIG. 2.

FIG. 12 shows an example computing device 801 of medical digital imaging system 102. As illustrated, example computing device 801 includes at least one central processing unit ("CPU") 802, memory 803, and a system bus 822 that couples memory 803 to the CPU 802. Memory 803 includes system memory 808 and mass storage device 814. System memory 808 includes a random access memory ("RAM") 810 and a read-only memory ("ROM") 812. A basic input/output system that contains the basic routines that help to transfer information between elements within the example computing device 801, such as during startup, is stored in the ROM 812. Memory 803 further includes mass storage device 814. Mass storage device 814 is able to store software applications 816, operating system 818, and data.

Mass storage device 814 is connected to CPU 802 through a mass storage controller (not shown) connected to the system bus 822. Mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central processing unit can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. The network 110 may be a protected network. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed in this disclosure. For example, the mass storage device 814 and/or the RAM 810 can store software instructions that, when executed by the CPU 802, cause the medical digital imaging system 102 to determine pupil edge pixels in digital images.

Although various embodiments are described herein, those of ordinary skill in the art will understand that many modifications may be made thereto within the scope of the present disclosure. Accordingly, it is not intended that the scope of the disclosure in any way be limited by the examples provided.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A method of identifying a pupil edge in a digital image, the method comprising:
  receiving a digital pupil image;
  generating a mean first portion pixel intensity of a first portion of the digital pupil image;
  generating a mean second portion pixel intensity of a second portion of the digital pupil image;
  averaging the mean first portion pixel intensity and the mean second portion pixel intensity to generate an average pixel intensity;
  determining a modified standard deviation, including:
    calculating a standard deviation of a pixel intensity for each pixel within the first portion and the second portion; and
    multiplying the standard deviation by a multiplier;
  generating a threshold value by summing the average pixel intensity and the modified standard deviation; and
  using the threshold value, identifying the pupil edge in the digital pupil image.

2. The method according to claim 1, wherein generating the mean first portion pixel intensity includes:
  for each pixel within the first portion, determining a first portion pixel intensity;
  summing the first portion pixel intensity for each pixel within the first portion, thereby generating a summed first portion pixel intensity; and
  generating a first portion mean pixel intensity by dividing the summed first portion pixel intensity by a number of pixels within the first portion of the digital pupil image.

3. The method according to claim 2, wherein generating the mean second portion pixel intensity includes:
  for each pixel within the second portion, determining a second portion pixel intensity;
  summing the second portion pixel intensity for each pixel within the second portion, thereby generating a summed second portion pixel intensity; and
  generating a second portion mean pixel intensity by dividing the summed second portion pixel intensity by a number of pixels within the second portion of the digital pupil image.

4. The method according to claim 1, wherein the multiplier is more than 1 but no greater than 3.

5. The method according to claim 1, further comprising obtaining a pixel grid size having a pixel grid width and a pixel grid length,
  wherein the first portion has a first portion length and a first portion width, the first portion length being equal to the pixel grid length and the first portion width being equal to the pixel grid width; and
  wherein the second portion has a second portion length and a second portion width, the second portion length being equal to the pixel grid length and the second portion width being equal to the pixel grid width.

6. The method according to claim 5, wherein the pixel grid width is at least 1 pixel but no more than 3 pixels; and
  wherein the pixel grid length is at least 30 pixels but no more than 34 pixels.

7. The method according to claim 1, wherein the first portion is in a side region of the digital pupil image; and
  wherein the second portion is in an opposite side region of the digital pupil image.

8. The method according to claim 7, wherein the first portion is centered in the side region of the digital pupil image; and
  wherein the second portion is centered in the opposite side region of the digital pupil image.

9. The method according to claim 1, wherein the digital pupil image is 71 pixels by 71 pixels.

10. The method according to claim 1, further comprising obtaining a candidate region of the digital pupil image, the candidate region being an area of the digital pupil image that includes a pupil.

11. The method according to claim 10, wherein the candidate region is 11.5 mm by 11.5 mm.

12. The method according to claim 10, wherein the candidate region has a length between 69 and 73 pixels and a width between 69 and 73 pixels.

13. A method for identifying a pupil in a digital image, the method comprising:
  receiving a digital pupil image;
  identifying a first portion of the digital pupil image;
  identifying a second portion of the digital pupil image;
  determining a pixel intensity for each pixel within the first portion and each pixel within the second portion;
  determining a mean pixel intensity by calculating the mean of the pixel intensity for each pixel within the first portion and each pixel within the second portion;
  determining a modified standard deviation, including:
    calculating a standard deviation of the pixel intensity for each pixel within the first portion and the second portion; and
    multiplying the standard deviation by a multiplier;
  generating a threshold value by summing the mean pixel intensity and the modified standard deviation;
  using the threshold value, identifying a pupil edge in the digital pupil image; and
  using the pupil edge, identifying the pupil in the digital pupil image.

14. The method according to claim 13, further comprising obtaining a pixel grid size having a pixel grid width and a pixel grid length,
  wherein the first portion has a first portion length and a first portion width, the first portion length being equal to the pixel grid length and the first portion width being equal to the pixel grid width; and
  wherein the second portion has a second portion length and a second portion width, the second portion length being equal to the pixel grid length and the second portion width being equal to the pixel grid width.

15. The method according to claim 14, further comprising obtaining a candidate region of the digital pupil image, the candidate region being an area of the digital pupil image that includes the pupil,
  wherein the candidate region has a length between 69 and 73 pixels and a width between 69 and 73 pixels.

16. The method according to claim 15, wherein the multiplier is more than 1 but no greater than 3;
  wherein the pixel grid width is at least 1 pixel but no more than 3 pixels; and
  wherein the pixel grid length is at least 28 pixels but no more than 36 pixels.

17. A medical imaging system, comprising:
  an illumination assembly including a near-infrared lighting unit;
  a digital camera assembly;
  a processing unit; and memory storing instructions that, when executed by the processing unit, cause the medical imaging system to:
illuminate the near-infrared lighting unit;
receive a digital pupil image with the digital camera assembly;
obtain a pixel grid size having a pixel grid width and a pixel grid length;
generate a mean first portion pixel intensity, including evaluating a first portion of the digital pupil image, a first portion length being equal to the pixel grid length and a first portion width being equal to the pixel grid width;
generate a mean second portion pixel intensity, including evaluating a second portion of the digital pupil image, a second portion length being equal to the pixel grid length and a second portion width being equal to the pixel grid width,
average the mean first portion pixel intensity and the mean second portion pixel intensity, thereby generating an average pixel intensity;
determine a modified standard deviation, including:
calculate a standard deviation of a pixel intensity for each pixel within the first portion and the second portion; and
multiply the standard deviation by a multiplier;
generate a threshold value by summing the average pixel intensity and the modified standard deviation; and
using the threshold value, identify a pupil edge in the digital pupil image.

18. The medical imaging system according to claim 17, wherein generating the mean first portion pixel intensity includes:
for each pixel within the first portion, determining a first portion pixel intensity;
summing the first portion pixel intensity for each pixel within the first portion, thereby generating a summed first portion pixel intensity;
generating a first portion mean pixel intensity by dividing the summed first portion pixel intensity by a number of pixels within the first portion of the digital pupil image; and
wherein generating the mean second portion pixel intensity includes:
for each pixel within the second portion, determining a second portion pixel intensity;
summing the second portion pixel intensity for each pixel within the second portion, thereby generating a summed second portion pixel intensity; and
generating a second portion mean pixel intensity by dividing the summed second portion pixel intensity by a number of pixels within the second portion of the digital pupil image.

19. The medical imaging system according to claim 18, the memory further storing instructions that, when executed by the processing unit, cause the medical imaging system to:
using the pupil edge, generate a best fit circle approximating a pupil size.

20. The medical imaging device according to claim 18, wherein the multiplier is more than 1 but no greater than 3;
wherein the pixel grid width is at least 1 pixel but no more than 3 pixels;
wherein the pixel grid length is at least 30 pixels but no more than 34 pixels;
wherein the first portion is centered in a side region of the digital pupil image; and
wherein the second portion is centered in an opposite side region of the digital pupil image.

\* \* \* \* \*